United States Patent [19]

Kessler et al.

[11] Patent Number: 4,650,788
[45] Date of Patent: Mar. 17, 1987

[54] NOVEL PEPTIDES HAVING AN IMMUNOSTIMULATING ACTION, PROCESSES FOR THEIR PREPARATION AND THEIR USE

[75] Inventors: Horst Kessler, Schwalbach; Bernhard Kutscher, Frankfurt am Main; Rainer Obermeier, Hattersheim am Main; Hubert Müllner, Kelkheim, all of Fed. Rep. of Germany

[73] Assignee: Hoechst Aktiengesellschaft, Fed. Rep. of Germany

[21] Appl. No.: 636,673

[22] Filed: Aug. 1, 1984

[30] Foreign Application Priority Data

Aug. 3, 1983 [DE] Fed. Rep. of Germany ....... 3327927
Jan. 18, 1984 [DE] Fed. Rep. of Germany ....... 3401545

[51] Int. Cl.[4] .................. A61K 37/02; C07K 5/12
[52] U.S. Cl. ...................................... 514/11; 530/321
[58] Field of Search .................. 260/112.5 R; 514/11; 530/321

[56] References Cited

U.S. PATENT DOCUMENTS 4,298,523 11/1981 Heavner .............................. 530/330
4,505,853 3/1985 Goldstein et al. ........... 260/112.5 R
4,547,489 10/1985 Goldstein et al. ..................... 514/11

FOREIGN PATENT DOCUMENTS 0037246 3/1981 European Pat. Off. .
2804566 5/1979 Fed. Rep. of Germany .
1565032 7/1978 United Kingdom .

OTHER PUBLICATIONS

J. Exp. Med. vol. 148, (1978) 996–1006.

Primary Examiner—Delbert R. Phillips
Attorney, Agent, or Firm—Finnegan, Henderson, Farabow, Garrett & Dunner

[57] ABSTRACT

The invention relates to cyclopeptides of the formula I

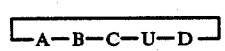
(I)

in which A denotes Lys, D-Lys, Arg or D-Arg, B denotes Lys, D-Lys, Arg or D-Arg, C denotes Asp, D-Asp, Glu or D-Glu, U denotes Val or D-Val and D denotes Tyr, D-Tyr, Trp, D-Trp, Phe or D-Phe, 1 to 4 of the radicals A, B, C, U and D being in the L-configuration and the remaining radicals being in the D-configuration, processes for their preparation, their use and peptidic precursors and processes for their preparation.

8 Claims, No Drawings

NOVEL PEPTIDES HAVING AN IMMUNOSTIMULATING ACTION, PROCESSES FOR THEIR PREPARATION AND THEIR USE

Several peptides (for example thymosin and thymopoietin II), which contribute to differentiation ("maturation") of thymus-dependent lymphocytes (T cells) have been isolated from thymus extracts. A part sequence of thymopoietin II, Arg-Lys-Asp-Val-Tyr, also exhibits a thymopoietin-like action in the corresponding test systems, for example the rosette test (Science (1979) 204, 1309 to 1310).

Besides the rosette test mentioned, the PHA stimulation test and the plaque-forming cell test (PFC test), which is specific for B lymphocytes, are also suitable for investigating the influence of smaller peptides on lymphocytes.

In the PHA stimulation test (PHA=phytohemagglutinin) or the lymphocyte transformation test, conclusions as to the number of mature, i.e. stimulatable, lymphocytes are drawn not via investigation of the surface antigens but by the function test for ability to be stimulated by the plant lectin PHA. The lymphocytes (T cells) are stimulated to vesicular transformation by the lectin, in the same way as by bacterial or viral antigens. This leads to proliferation, either directly or by the release of lymphokins. The incorporation of the radiolabeled thymidine within a certain time is then a measure of the number of stimulated cells. Only the mature or immunologically potent T cells are stimulated. The influence of a substance on lymphocyte maturation can therefore be monitored with this test. However, the stimulation must be sub-optimum, since other sub-populations of lymphocytes are also stimulated at higher concentrations and the effect can no longer be observed. The peptides to be investigated have been added to the culture medium in various concentrations. They are present throughout the entire duration of the test (up to 72 hours).

In the PFC test, cell cultures of freshly dissected spleens of mice ($2 \times 10^7$ spleen cells per ml) are placed in RPMI 1640 and 30 µl of fetal calf serum (FCS) per ml of cell culture. The in vitro immunization is effected with $5 \times 10^7$ sheep erythrocytes/ml. The test cell cultures are incubated daily with the corresponding dose of the test substance.

After a running time of 5 days, the cells are centrifuged off and washed with medium RPMI 1640 and the direct PFC test is carried out. For this, the cells are mixed with a 10% sheep erythrocyte suspension in an agarose solution and the mixture is poured onto a flat surface. In the layer of gel formed, the stimulated lymphocytes release antibodies during subsequent incubation, and these diffuse into the environment and attach themselves to the sheep erythrocytes therein. After addition of guinea pig complement, the red blood cells lyse. Light-colored round spots which can be seen with the naked eye form in the reddish-brown gel, i.e. the hemolysis areolas of the plaques. An antibody-producing cell is found in the center of such hemolysis areolas. The number of lymphoid cells which form specific immunoglobulins can consequently be equated with the numbers of plaques found.

Novel cyclic peptides have now been found which, surprisingly, have a superior action to the known action of the linear peptide Arg-Lys-Asp-Val-Tyr.

The invention relates to cyclopeptides of the formula I

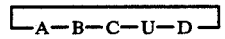  (I)

in which
- A denotes Lys, D-Lys, Arg or D-Arg,
- B denotes Lys, D-Lys, Arg or D-Arg,
- C denotes Asp, D-Asp, Glu or D-Glu,
- U denotes Val or D-Val and
- D denotes Tyr, D-Tyr, Trp, D-Trp, Phe or D-Phe, 1 to 4 of the radicals A, B, C, U and D being in the L-configuration and the remainder being in the D-configuration, and to physiologically acceptable salts thereof.

Preferred cyclopeptides of the formula I are those in which U denotes Val, and furthermore those in which, in formula I,
- A denotes D-Lys or Arg,
- B denotes Lys, D-Lys or Arg,
- C denotes Asp or Glu,
- U denotes D-Val and
- D denotes Tyr, Trp or D-Phe.

The invention furthermore relates to a process for the preparation of these cyclopeptides, which comprises cyclizing linear peptide derivatives of the formula II

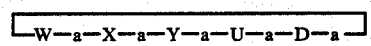  (II)

in which
- W denotes Lys ($R^1$), D-Lys ($R^1$), Arg ($R^2$) or D-Arg ($R^2$),
- X denotes Lys ($R^1$), D-Lys ($R^1$), Arg ($R^2$) or D-Arg ($R^2$) and
- Y denotes Asp ($R^3$), D-Asp ($R^3$), Glu ($R^3$) or D-Glu ($R^3$) and
- U and D are as defined above, and in which
- $R^1$ represents a urethane-protective group,
- $R^2$ represents a protective group for the guanidino function and
- $R^3$ represents an ester-protective group, and one of the radicals a denotes the C-terminal OH together with the N-terminal H (a=—OH H—) of two aminoacid radicals and the remaining four radicals a each denote peptide bonds, and then removing, in a manner which is known per se, the protective groups from the resulting compounds of the formula II, in which W, X, Y, U, D, $R^1$, $R^2$ and $R^3$ are as defined above, all the five radicals a represent peptide bonds and 1 to 4 of the radicals W, X, Y, U and D are in the L-configuration and the remainder are in the D-configuration, and, if appropriate, converting the resulting cyclopeptides of the formula I into their physiologically acceptable salts.

The linear cyclization precursors of the formula II are understood as meaning peptides of the following formulae III to VII

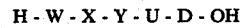  (III)

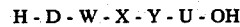  (IV)

  (V)

H - Y - U - D - W - X - OH　　　　(VI)

X - X - Y - U - D - W - OH　　　　(VII)

in which W, X, Y, U, D, R$^1$, R$^2$ and R$^3$ are as defined above.

The peptides of the formulae II to VI are preferably cyclized in the presence of coupling reagents, such as DCC or EDCI, with addition of DMAP.

Examples of urethane-protective groups of the ε-amino function of the lysine are Fmoc, Fcboc, Z, Boc, Ddz, Bpoc, Z-(NO$_2$), Pyoc, Dobz, Moc, Mboc, Iboc, Adoc, Adpoc, Msc or Pioc; Z or Boc is preferred. These amino-protective groups are removed with acids or bases or by reduction (cf. Kontakte Merck 3/79, page 14 et seq.).

Examples of protective groups for the guanidino group of the arginine are NO$_2$, tosyl, Boc, Z, mesitylene-2-sulfonyl (Mts) and the like. The protective groups can be split off hydrolytically or hydrogenolytically (cf. Kontakte Merck 1/80, pages 23 and 30).

The COOH side functions of Asp and Glu are blocked in the form of alkyl esters, preferably methyl, ethyl or tert.-butyl esters, or as benzyl esters or modified benzyl esters (p—NO$_2$, p—Cl, p—Br and the like). Deblocking is effected by alkaline or acid hydrolysis or hydrogenation (cf. Kontakte Merck 3/79, pages 14 and 20). The allyl ester, which is easy to remove by reaction with metal catalysts, is also suitable (cf. Angew. Chem. 96, 49 (1984)).

The invention furthermore relates to peptides of the formula II

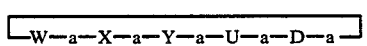　　(II)

in which W, X, Y, U, D, R$^1$, R$^2$ and R$^3$ have the meanings defined above and (a) all five radicals a represent peptide bonds or (b) one of the radicals a denotes a C-terminal OH together with an N-terminal H (a=—OH H—) of two aminoacid radicals W and X, X and Y, Y and U, U and D, or D and W, and the remaining four radicals a each denote peptide bonds.

The linear peptides of the formula II (one radical a=—OH H—) can be prepared either conventionally or by means of solid phase synthesis.

In the conventional peptide synthesis of the above linear peptides, build-up through fragments (convergent) may be the most rational route. A linear, protected pentapeptide is thereby obtained, from which the linear peptides of the formulae III–VII can be obtained by splitting-off the C- and N-terminal protective groups. In the first example, Trp occupies the advantageous N-terminal position and is thus exposed to a minimum number of splitting off reactions on protective groups, which frequently lead to side reactions in the case of Trp. Tyr could also be used in unprotected form in this position, since the minimum number of coupling steps or of splitting-off reactions on protective groups makes a reaction of the phenolic OH group improbable.

The selection of the protective groups and the synthesis strategy are determined by the nature and configuration of the aminoacids and by the nature of the coupling and cyclization conditions.

The peptides of the formula I according to the invention contain a few polyfunctional aminoacids which require an increased use of the protective group technique (orthogonal protective group tactics). In conventional peptide synthesis (by fragment condensation), three protective groups which can be split off selectively are therefore required to build up the linear precursors of the formulae III–VII. All the polyfunctional aminoacids are used in orthogonally protected form, i.e. with a permanent protective group in the side chain and a C-terminal or N-terminal protective group which can be split selectively to this group, for building up the peptide chain. The aminoacids without side chain functionality are used in C- or N-terminally protected form. The corresponding aminoacid derivatives are linked using a coupling reagent, such as PPA or DCC. After selective splitting off of one of the C- or N-terminal protective groups of the dipeptide fragment, the missing C- or N-terminally protected aminoacid derivatives or fragments prepared in the same manner are condensed on until the desired, fully protected linear pentapeptide has been prepared. Splitting off of the terminal protective groups in as far as possible one step then gives the linear precursors III–VII.

The C-terminal and N-terminal protective groups are chosen so that only one splitting-off step is necessary for the preparation of the linear, de-protected pentapeptides of the formulae III–VII from the fully protected peptide. Such a combination is, for example, the Boc protective group and the tert.-butyl ester, both of which can be split off in one step, for example by trifluoroacetic acid.

Since global de-protection of the side chain functions appears advantageous after the cyclization, protective groups with the same instability towards particular splitting-off reagents are preferably used there. Thus, for example, the ε-Z-protective group for lysine, the β-benzyl ester for Asp and the ω-NO$_2$ group on the Arg can be split off in one step hydrogenolytically with the aid of a hydrogenation catalyst (for example palladium on charcoal).

For cyclization of the linear peptides according to formula III–VII, a novel cyclization method has been developed, since other cyclization methods gave only unsatisfactory amounts of the pentapeptides of the formula I according to the invention. In the novel process, the linear precursors according to formulae III–VII are dissolved in aprotic solvents, such as DMF, CH$_2$Cl$_2$, CHCl$_3$, THF, dioxane or mixtures thereof.

In the case of salts of the linear compounds of the formulae III–VII, these are neutralized by addition of one equivalent of a base. Cyclization reagents which can be used are, for example, DCC or EDCI (about 20 equivalents) in combination with about 10 equivalents of the acylation catalyst DMAP. Both substances are added to the reaction solution at −15° C., and this mixture is left at between −2° C. and +25° C. for 6 days. The crude product can then be purified, for example, by gel chromatography or the like.

After the cyclization, the remaining protective groups are split off from the resulting peptides of the formula II (all the radicals a denote peptide bonds).

In the cyclization of the linear peptides of the formulae III–VII, in the cases where the N- and C-terminal aminoacids of these linear precursors have the same absolute configuration, a configuration reversal on the C-terminal aminoacid will take place.

Equation:

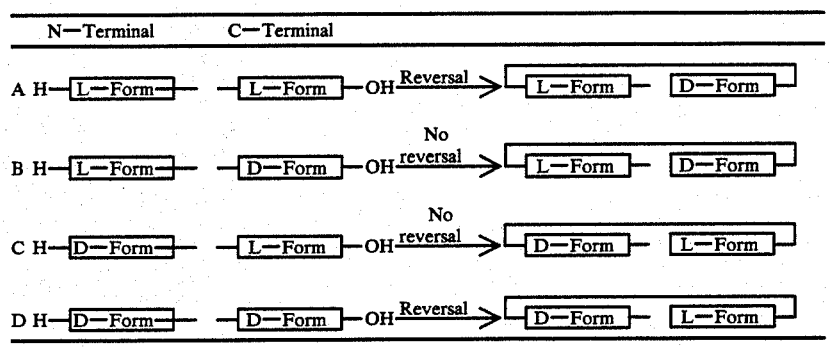

The examples which follow illustrate this synthesis principle with the aid of a few selected compounds.

hydroxides or alkaline earth metal hydroxides or physiologically acceptable amines.

TABLE 1

| Educts | Products of DCC (EDCI)/DMAP cyclization |
| --- | --- |
| (a) H—Try—Arg(NO₂)—Lys(Z)—Glu(OBzl)—Val—OH | cyclo-[-Tyr—Arg(NO₂)—Lys(Z)—Glu(OBzl)—D-Val—] |
| (b) H—Try—Arg(NO₂)—Lys(Z)—Asp(OBzl)—Val—OH | cyclo-[-Tyr—Arg(NO₂)—Lys(Z)—Asp(OBzl)—D-Val—] |
| (c) H—Trp—Arg(NO₂)—Lys(Z)—Glu(OBzl)—Val—OH | cyclo-[-Tyr—Arg(NO₂)—Lys(Z)—Glu(OBzl)—D-Val—] |
| (d) H—Trp—Arg(NO₂)—Lys(Z)—Asp(OBzl)—Val—OH | cyclo-[-Tyr—Arg(NO₂)—Lys(Z)—Asp(OBzl)—D-Val—] |
| (e) H—Tyr—Arg(NO₂)—D-Lys(Z)—Glu(OBzl)—Val—OH | cyclo-[-Tyr—Arg(NO₂)—D-Lys(Z)—Glu(OBzl)—D-Val—] |
| (f) H—Tyr—Arg(NO₂)—D-Lys(Z)—Glu(OBzl)—Val—OH | cyclo-[-Tyr—Arg(NO₂)—D-Lys(Z)—Glu(OBzl)—D-Val—] |
| (g) H—Arg(NO₂)—Lys(Z)—Asp(OBzl)—Val—Tyr—OH | cyclo-[-Arg(NO₂)—Lys(Z)—Asp(OBzl)—Val—D-Try—] |
| (h) H—Tyr—Arg(NO₂)—Lys(Z)—Glu(OBzl)—D-Val—OH | cyclo-[-Tyr—Arg(NO₂)—Lys(Z)—Glu(OBzl)—D-Val—] |
| (i) H—Tyr—Arg(NO₂)—Lys(Z)—Asp(OBzl)—D-Val—OH | cyclo-[-Tyr—Arg(NO₂)—Lys(Z)—Asp(OBzl)—D-Val—] |
| (j) H—D-Lys(Z)—Arg(NO₂)—Glu(OBzl)—Val—Tyr—OH | cyclo-[-D-Lys(NO₂)—Arg(NO₂)—Glu(OBzl)—Val—Tyr] |
| (k) H—D-Lys(Z)—Arg(NO₂)—Asp(OBzl)—Val—Tyr—OH | cyclo-[-D-Lys(NO₂)—Arg(NO₂)—Asp(OBzl)—Val—Tyr] |
| (l) H—D-Phe—Arg(NO₂)—Lys(Z)—Glu(OBzl)—Val—OH | cyclo-[-D-Phe—Arg(NO₂)—Lys(Z)—Glu(OBzl)—Val—] |

As can be seen from the above equation, the cyclization products have the same configurations on the cyclization site independently of whether A or B was used as the starting substance. Corresponding statements apply to C and D.

The cyclopeptides listed above under (a)–(g) contain, after the cyclization with DCC(EDCI)/DMAP, the C-terminal aminoacid in the linear precursor as a D-aminoacid. The linear educts here contain no D-aminoacid or a D-aminoacid in the center of the sequence.

The chirality of the C-terminal aminoacid has been determined as a D-aminoacid in the cyclopeptides under (a) and (f) by chiral aminoacid analysis. The NMR spectra leave no doubt that the cyclopeptides under (b)–(e) can also be concluded from these data. Ignoring the configuration, the cyclopeptide under (g) has the same sequence as that under (b), but the other cyclization site leads to another stereoisomeric product.

Insertions of the above cyclopeptides already contain D-aminoacids in the linear educts in the C- or in the N-terminal position. No racemization or inversion of the C-terminal aminoacids is found here. The cyclopeptides under (h) and (i) correspond to the cyclopeptides under (a) and (b) prepared from all L-aminoacid precursors. The cyclopeptide in position (j) shows no D-Tyr in the chiral aminoacid analysis. The cyclopeptide in position (l) shows clear similarities with the cyclopeptide in position (g) in the ¹H-NMR spectrum. The cyclopeptides under (a), (j) and (l) are also obtained by azide cyclization (low degree of racemization).

Physiologically acceptable salts of the cyclopeptides of the formula I according to the invention are understood as meaning, in particular, acid addition salts with inorganic acids, such as HCl, HNO₃, H₂SO₄ or H₃PO₄, or organic acids, such as tartaric acid, citric acid or maleic acid, or base addition salts with alkali metal hydroxides or alkaline earth metal hydroxides or physiologically acceptable amines.

The cyclopeptides according to the invention have been tested for their lymphocyte-stimulating action in the plaque-forming cell assay (PFC test) and in the phytohemagglutinin stimulation test (PHA test).

Possible degradation of the peptides by serum or lymphocyte proteases is not taken into consideration in these investigations.

The compounds according to the invention can be used for the treatment of immunodeficiencies, viral, fungoidal and chronic bacterial infections and autoimmune diseases and for the therapy of diseases which are caused by cells with immunologically relevant changes in the cell membrane characteristics.

The invention furthermore relates quite generally to the use of the peptides mentioned for influencing maturation of T lymphocytes, and to agents which contain these peptides as the active ingredient.

The peptides according to the invention can be used intravenously, subcutaneously or intranasally. In adults of normal weight, the dosage on parenteral administration is 0.001–10 mg, and that on intranasal administration is 0.01–10 mg, per individual dose. In serious cases, it can also be increased, since no toxic properties have as yet been observed. It is also possible to reduce the dose.

The compounds according to the invention can be administered intranasally or parenterally in a corresponding pharmaceutical formulation. For an intranasal use form, the compounds are mixed with the additives customary for this purpose, such as stabilizers or inert diluents, and are brought into suitable administration forms, such as aqueous, alcoholic or oily suspensions or aqueous, alcoholic or oily solutions, by customary methods. Examples of possible oily excipients or solvents are vegetable or animal oils, such as sunflower oil or cod liver oil.

For subcutaneous or intravenous administration, the active compounds or physiologically acceptable salts thereof are dissolved, suspended or emulsified, if desired with the substances customary for this purpose, such as solubilizing agents, emulsifiers or other additives.

Examples of possible solvents for the novel active compounds and corresponding physiologically acceptable salts are: water, physiological saline solutions or alcohols, for example ethanol, propanediol or glycerol, and in addition also sugar solutions, such as glucose or mannitol solutions, or also a mixture of the various solvents mentioned.

The test results which follow (Table 2) give a selection of the biological activity of the peptides according to the invention in the PFC and PHA tests.

TABLE 2

Dosage 100 ng/substance/1 ml of cell culture

| | PFC/$10^6$ cells | PHA stimulation index 10 μg of PHA/ 1 ml 72 hours |
|---|---|---|
| Control (untreated) | 221 ± 30 | 1.00 |
| Arg—Lys—Asp—Val—Tyr | 298 ± 43 | 1.05 |
| cyclo-(Arg—Lys—Asp—D-Val—Tyr) | 401 ± 64 | 1.69 |
| cyclo-(Arg—Lys—Glu—D-Val—Tyr) | 687 ± 73 | 1.92 |
| cyclo-(D-Lys—Arg—Glu—Val—Tyr) | 317 ± 41 | 1.15 |
| cyclo-(Arg—Lys—Glu—D-Val—Trp) | 369 ± 54 | 1.25 |
| cyclo-(Arg—Lys—Asp—D-Val—Trp) | 312 ± 58 | — |
| cyclo-(D-Lys—Arg—Asp—Val—Tyr) | 341 ± 43 | — |
| cyclo-(Arg—Lys—Glu—Val—D-Phe) | 250 ± 31 | — |

The following synthesis examples are intended for further illustration, without the invention being restricted to these examples:

EXAMPLE 1

Preparation of cyclo-(Arg-Lys-Asp-D-Val-Tyr).2HOAc (1) according to synthesis scheme I (a) Boc-Arg(NO$_2$)-Lys(Z)-OMe (3)

8.25 g (25 mmol) of H-Lys(Z)-OMe.HCl and 7.98 g (25 mmol) of Boc-Arg(NO$_2$)-OH are suspended in 100 ml of CH$_2$Cl$_2$, the suspension is cooled to −15° C. and 12.94 ml (0.118 mol) of NMM are added. 22 g (50.5 mmol) of PPA solution (50% in CH$_2$Cl$_2$, 0.88 g/mmol) are then added dropwise under an N$_2$ atmosphere. After the mixture has been warmed slowly, it is stirred at room temperature for 2 days.

The solvent is stripped off on a rotary evaporator and the residue is partitioned between 300 ml of EE and 150 ml of sat. NaHCO$_3$ solution. The organic phase is washed twice with 80 ml of sat. NaHCO$_3$ solution each time, three times with 80 ml of 5% strength citric acid solution each time and again with 80 ml of sat. NaCl solution. The combined EE phases are dried over MgSO$_4$, the solvent is stripped off and the residue is dried to give a solid foam.

Yield: 13.8 g (93%); R$_f$A 0.31; B 0.54; C 0.71;
[α]$_D^{20}$= −7.44° (c=1, abs. MeOH)

| C$_{26}$H$_{21}$B$_7$O$_9$ (595.35) | calculated | C 52.44 | H 6.94 | N 16.47 |
|---|---|---|---|---|
| | found | 52.33 | 6.82 | 16.20 |

(b) Ddz-Asp(OBzl)-Val-OBut (4)

The peptide coupling is carried out by the PPA method as described for (a). Batch: 13.4 g (30 mmol) of Ddz-Asp(OBzl)-OH and 10.36 g (30 mmol) of H-Val-OBut.TsOH.

The product is obtained as an oil.
Yield: 16 g (88%); R$_f$A 0.68; B 0.69; C 0.75

(c) H-Arg(NO$_2$)-Lys(Z)-OMeHCl (5)

To split off the Boc protective group, 9.53 g (16 mmol) of 3 are stirred with 160 ml of 2 N HCl/MeOH at room temperature for 2 hours. The solution is then concentrated and the residue is taken up in MeOH and evaporated again, this procedure being repeated several times. The product is recrystallized from EtOH/diethyl ether.

Yield: 8.2 g (97%)
M.p.: 165°–168° C.; R$_f$A 0.0; B 0.41; C 0.34;
[α]$_D^{20}$= +9.61°
(c=1, abs. MeOH)

| C$_{21}$H$_{32}$N$_7$O$_7$Cl (529.74) | calculated | C 47.61 | H 6.08 | N 18.51 |
|---|---|---|---|---|
| | found | 47.90 | 6.30 | 18.55 |

(d) H-Asp(OBzl)-Val-OBut.TFA (6)

To split off the Ddz protective group, 12 g (20 mmol) of 4 are dissolved in 130 ml of CH$_2$Cl$_2$, and 4.6 ml (60 mmol) of TFA are added (3.5% of TFA/CH$_2$Cl$_2$).

The solution is stirred at room temperature for 30 minutes and the solvent is stripped off. The residue is recrystallized from diethyl ether/petroleum ether.
Yield: 9.15 g (93%);
M.p.: 113°–116° C.; R$_f$A 0.25; B 0.68; C 0.70;
[α]$_D^{20}$= −3.56° (c=1, abs. MeOH)

(e) Boc-Tyr-Arg(NO$_2$)-Lys(Z)-OMe (7)

The peptide coupling is carried out by the PPA method as described under (a).
Batch: 5.55 g (12 mmol) of Boc-Tyr-OH.DCHA and 6.35 g (12 mmol) of 5.
The product is recrystallized from EtOH/diethyl ether.
Yield: 8.65 g (95%);
M.p.: 128°–130° C.; R$_f$A 0.15; B 0.80; C 0.85;
[α]$_D^{20}$= −6.8° (c=1, abs. MeOH)

(f) Boc-Tyr-Arg(NO$_2$)-Lys(Z)-OH (8)

To hydrolyze the methyl ester, 8.5 g (11 mmol) of 7 are dissolved in 33 ml of MeOH, and 26 ml of 1 N NaOH are added. The aqueous solution is acidified to pH 2 with 2 N HCl and is extracted three times with 80 ml of EE each time. The aqueous phase is saturated with NaCl and extracted a further three times with 80 ml of EE each time. The combined organic phases are dried over Na$_2$SO$_4$. The solvent is removed and the residue is dried to give a solid foam.
Yield: 7.4 g (90%); R$_f$A 0.19; B 0.57; 0.48;
[α]$_D^{20}$= −5.66° (c=1, abs. MeOH)

(g) Boc-Tyr-Arg(NO$_2$)-Lys(Z)-Asp(OBzl)-Val-OBut (9)

The peptide coupling is carried out by the PPA method as described for (a).
Batch: 4.46 g (6 mmol) of 8 and 3.25 g (6.6 mmol) of 6. The crude product obtained after working up is purified by gel chromatography on Sephadex LH 20 with DMF as the eluting agent. The product is recrystallized from EtOH/diethyl ether.

Yield: 3.6 g (54%);
M.p.: 108°–111° C.; $R_f$ A 0.0; B 0.91; C 0.84;
$[\alpha]_D^{20} = -19.4°$ (c=1, abs. MeOH)

| $C_{54}H_{76}N_{10}O_{15}$ (1105.18) | calculated | C 58.69 | H 6.92 | N 12.67 |
|---|---|---|---|---|
| | found | 58.44 | 6.78 | 12.54 |

(h) H-Tyr-Arg(NO$_2$)-Lys(Z)-Asp(OBzl)-Val-OH·TFA (10)

For simultaneous splitting off of the Boc and tert.-butyl ester protective groups, 7.4 ml (96 mmol) of TFA are added to 2.65 g (2.4 mmol) of 9 and the mixture is stirred under an N$_2$ atmosphere at room temperature for 10 minutes. The solution is taken up in 50 ml of CH$_2$Cl$_2$ and the mixture is evaporated. The product is then recrystallized from MeOH/diethyl ether and dried over KOH.
Yield: 2.39 g (95%);
M.p.: 158°–160° C., $R_f$ A 0.0; B 0.63; C 0.57

(i) cyclo-(Tyr-Arg(NO$_2$)-Lys(Z)-Asp(OBzl)-D-Val) (11)

2.1 g (2.0 mmol) of 11 are dissolved in a mixture of 300 ml of DMF and 1.7 liters of CH$_2$Cl$_2$ (=1 mmol of peptide per liter of solvent) and the solution is cooled to −15° C. 0.18 ml (2 mmol) of NMM and 2.44 g (20 mmol) of DMAP are added, and 3.83 g (20 mmol) of EDCI, dissolved in 25 ml of DMF, are added dropwise to the solution. The reaction solution is left to stand at −2/5° C. for 3 days and is then cooled to −15° C. and subsequently activated with 3.83 g (20 mmol) of EDCI. After two days at −2/+5° C. and one day at room temperature, the reaction solution is evaporated in vacuo. 300 ml of H$_2$O are added to the oily residue which remains after concentration, and the precipitate which has separated out is filtered off with suction. The resulting crude product is purified by gel chromatography on Sephadex LH 20 with DMF as the eluting agent, and the resulting product is recrystallized from DMF/MeOH/diethyl ether.
Yield: 558 mg (30%); m.p.: 238°–242° C. (decomposition);
$R_f$ A 0.0; B 0.88; C 0.92;
$[\alpha]_D^{20} = -45.58°$ (c=0.6 DMF)

| $C_{45}H_{58}N_{10}O_{12}$ (930.95) | calculated | C 58.05 | H 6.27 | N 15.05 |
|---|---|---|---|---|
| | found | 57.85 | 6.07 | 15.08 |

(j)
cyclo-(Tyr-Arg-Lys-Asp-D-Val)·2HOAc=cyclo-(Arg-Lys-Asp-D-Val-Tyr)·2HOAc (1)

To split off the side chain protective groups, 93 mg (0.1 mmol) of 11 are dissolved in 2 ml of MeOH and 5 ml of HOAc, 80 mg of catalyst (10% strength Pd-on-active charcoal) are added and hydrogenation is carried out at room temperature for 6 hours. The catalyst is filtered off, the solution is concentrated and the residue is dried over KOH.
Yield: 63 mg (81%); m.p.: 205° C. (decomposition);
$R_f$ A 0.0; B 0.22; C 0.0; D 0.43; aminoacid analysis: Asp 1.0; D-Val 1.01; Tys 0.81; Lys 1.00; Arg 0.97
content: 97%

EXAMPLE 2

Preparation of cyclo-(Arg-Lys-Glu-D-Val-Tyr)·2 HOAc (2) according to synthesis scheme I The desired compound is prepared by the same experimental procedures as described for Example 1. Compounds which are required for the preparation of 2 and have already been described in Example 1 are designated with the figures used therein.

(a) Ddz-Glu(OBzl)-Val-OBut (12)

The peptide coupling is carried out by the PPA method as described in Example 1 under (a).
Batch: 15.1 g (32 mmol) of Ddz-Glu(OBzl)-OH and 11.4 g (32 mmol) of H-Val-OBut.TsOH. The product is obtained as an oil.
Yield: 18.3 g (93%); $R_f$ A 0.70; B 0.65; C 0.78.

(b) H-Glu(OBzl)-Val-OBut.TFA (13)

Splitting off of the Ddz protective group is as described in Example 1 under (d).
Batch: 17.8 g (29 mmol) of 12, 6.7 ml (87 mmol) of TFA and 188 mmol of CH$_2$Cl$_2$.
The product is recrystallized from diethyl ether/petroleum ether.
Yield: 12.7 g (86%); m.p.: 132°–136° C.; $R_f$ A 0.2; B 0.65; C 0.70;
$[\alpha]_D^{20} = -0.23°$ (c=1, MeOH)

| $C_{23}H_{33}N_2O_7F_3$ (506.49) | calculated | C 54.54 | H 6.56 | N 5.58 |
|---|---|---|---|---|
| | found | 54.82 | 6.40 | 5.53 |

(c) Boc-Tyr-Arg(NO$_2$)-Lys(Z)-Gly(OBzl)-Val-OBut (14)

The peptide coupling and purification of the crude product are carried out as described in Example 1 under (g).
Batch: 5.96 g (18 mmol) of 8 and 5.06 g (10 mmol) of 13. The product is recrystallized from MeOH/EE.
Yield: 6.1 g (68%); m.p.: 149°–153° C.;
$R_f$ A 0.1; B 0.85; C 0.91;
$[\alpha]_D^{20} = -20.84°$ (c=1, MeOH)

| $C_{55}H_{78}N_{10}O_{15}$ (1119.2) | calculated | C 59.02 | H 7.02 | N 12.52 |
|---|---|---|---|---|
| | found | 58.78 | 6.94 | 12.29 |

(d) H-Tyr-Arg(NO$_2$-Lys(Z)-Glu(OBzl)-Val-OH.TFA (15)

The procedure is as described in Example 1 under (h).
Batch: 2.75 g (2.45 mmol) of 14 and 7.6 ml (98 mmol) of TFA.
Yield: 2.4 g (92%);
$R_f$ A 0.00; B 0.63; C 0.58.

(e) cyclo-(Tyr-Arg(NO$_2$)-Lys(Z)-Glu(OBzl)-D-Val) (16)

The cyclization is carried out as described in Example 1 under (i).
Batch: 2.4 g (2.2 mmol) of 15, 0.2 ml (2.2 mmol) of NMM, 2.68 g (22 mmol) of DMAP and 8.4 g (44 mmol) of EDCI.
The product obtained after gel chromatography is recrystallized from DMF/MeOH/diethyl ether.

Yield: 686 mg (33%); m.p.: 234°–238° C. (decomposition)

R$_f$A 0.00; B 0.80; C 0.86;

[α]$_D^{20}$ = −58.46° (c=0.26, DMF);

| | | | | |
|---|---|---|---|---|
| C$_{46}$H$_{60}$N$_{10}$O$_{12}$ (944.98) | calculated | H 58.47 | H 6.39 | N 14.82 |
| | found | 57.91 | 6.52 | 14.94 |

FAB-MS: 945

(f)

cyclo-(Tyr-Arg-Lys-Glu-D-Val).2HOAc=cyclo-(Arg-Lys-Glu-D-Val-Tyr).2HOAc (2)

Splitting off of the side chain protective groups is as described in Example 1 under (j).

Batch: 94 mg (0.1 mmol) of 16;

Yield: 65 mg (82%); m.p.: 140°–142° C. (decomposition);

R$_f$A 0.00; B 0.22; C 0.00; D 0.44.

Aminoacid analysis: Glu 0.98; D-Val 1.01; Tyr 0.84; content: 92%.

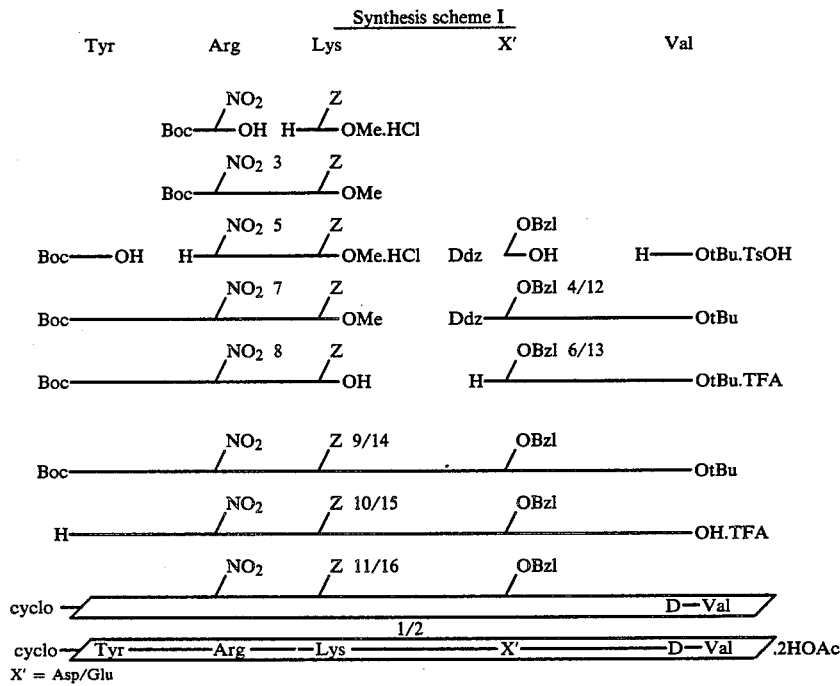

Abbreviations for protective groups and reagents

Boc=tert.-butoxycarbonyl
Bzl=benzyl
DCC=dicyclohexylcarbodiimide
DCHA=dicyclohexylamine
Ddz=α,α'-dimethyl-3,5-dimethoxybenzyloxycarbonyl
DMAP=4-dimethylaminopyridine
DMF=N,N-dimethylformamide
EDCI=1-ethyl-3-(3-dimethylaminopropyl)carbodiimide hydrochloride
EE=acetic ester (ethyl acetate)
EtOH=ethanol
HOAc=acetic acid
MeOH=methanol
NMM=N-methylmorpholine
OMe=methoxy
OBut=tert.-butoxy
PPA=n-propylphosphonic acid anhydride
TsOH=p-toluenesulfonic acid
Z=carbobenzoxycarbonyl Abbreviations in the text abs.=absolute
sat.=saturated
m.p.=melting point Eluting agents for thin-layer chromatography A chloroform/methanol/glacial acetic acid (95:5:3)
B n-butanol/glacial acetic acid/water (3:1:1)
C ethyl acetate/n-butanol/pyridine/water (20:10:3:5)
D methanol/glacial acetic acid (1:1)

We claim:

1. A cyclopeptide of the formula I

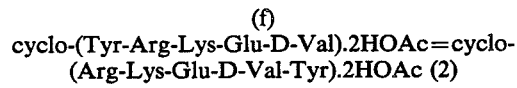   (I)

in which

A denotes Lys, D-Lys, Arg or D-Arg,
B denotes Lys, D-Lys, Arg or D-Arg,
C denotes Asp, D-Asp, Glu or D-Glu,
U denotes Val or D-Val and
D denotes Tyr, D-Tyr, Trp, D-Trp, Phe or D-Phe, 1 to 4 of the radicals A, B, C, U and D being in the L-configuration and the remainder being in the D-configuration, and a physiologically acceptable salt thereof.

2. A cyclopeptide as claimed in claim 1, in which

A denotes D-Lys or Arg,
B denotes Lys, D-Lys or Arg,
C denotes Asp or Glu,
U denotes D-Val and
D denotes Tyr, Trp or D-Phe.

3. A cyclopeptide as claimed in claim 1, wherein U denotes Val.

4. A peptide of the formula II

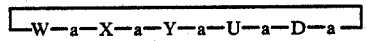 (II)

in which
- W denotes Lys ($R^1$), D-Lys ($R^1$), Arg ($R^2$) or D-Arg ($R^2$),
- X denotes Lys ($R^1$), D-Lys ($R^1$), Arg ($R^2$) or D-Arg ($R^2$) and
- Y denotes Asp ($R^3$), D-Asp ($R^3$), Glu ($R^3$) or D-Glu ($R^3$) and
- U and D are as defined in claim 1, and in which
- $R^1$ represents a urethane-protective group,
- $R^2$ represents a protective group for the guanidino function and
- $R^3$ represents an ester-protective group, and
- (a) all five radicals a represent peptide bonds or
- (b) one of the radicals a denotes a C-terminal OH together with an N-terminal H (a=—OH+H—) of two aminoacid radicals and the remaining four radicals a each denote peptide bonds.

5. A pharmaceutical composition for treating deficiencies of immunity comprising an effective amount of a compound or a mixture of compounds as claimed in claim 1 or a pharmaceutically acceptable salt thereof and a pharmaceutically acceptable carrier.

6. A method for influencing the maturing of lymphocytes which comprises treating said lymphocytes with a compound as claimed in claim 1.

7. A method of treating deficiencies of immunity by administering an effective amount of a compound as claimed in claim 1 or a pharmaceutically acceptable salt thereof.

8. A cyclopeptide as claimed in claim 1 in which
- A denotes Arg,
- B denotes Lys,
- C denotes Glu,
- U denotes D-Val and
- D denotes Tyr.

* * * * *